(12) United States Patent
Shimizu et al.

(10) Patent No.: US 6,514,234 B2
(45) Date of Patent: *Feb. 4, 2003

(54) DISPOSABLE DIAPER

(75) Inventors: Shingo Shimizu, Kagawa-ken (JP);
Toshiyasu Yoshioka, Kagawa-ken (JP);
Tomoko Tsuji, Kagawa-ken (JP)

(73) Assignee: Uni-Charm Corporation, Ehime-ken (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/366,775

(22) Filed: Aug. 4, 1999

(65) Prior Publication Data
US 2002/0065502 A1 May 30, 2002

(30) Foreign Application Priority Data
Aug. 5, 1998 (JP) .......................... 10-222135

(51) Int. Cl.[7] ................................................ A61F 13/15
(52) U.S. Cl. ......................... 604/385.27; 604/385.28
(58) Field of Search ...................... 604/385.01, 385.04, 604/385.21, 385.24, 385.27, 385.28

(56) References Cited

U.S. PATENT DOCUMENTS

| 4,741,941 A | * | 5/1988 | Englebert et al. ............. 428/71 |
| 4,743,246 A | * | 5/1988 | Lawson ....................... 604/385 |
| 5,601,544 A | | 2/1997 | Glaug |
| 5,916,206 A | * | 6/1999 | Otsubo et al. .......... 604/385.27 |
| 6,090,730 A | * | 7/2000 | Fujiwara et al. ............. 442/361 |
| 6,156,023 A | * | 12/2000 | Yoshioka ................ 604/385.29 |

FOREIGN PATENT DOCUMENTS

| EP | 0 269 221 | 6/1988 |
| EP | 0 833 002 | 4/1998 |
| JP | 3-80502 | 12/1991 |
| WO | WO 97 40225 | 10/1997 |

* cited by examiner

*Primary Examiner*—Glenn K. Dawson
*Assistant Examiner*—Jamisue A. Webb
(74) *Attorney, Agent, or Firm*—Lowe Hauptman Gilman & Berner, LLP

(57) ABSTRACT

A disposable diaper includes a pair of barrier flaps formed on an inner side of a disposable diaper. The barrier flaps are made of a spun bond nonwoven fabric of wick/sleeve type conjugated fibers having a polyethylen sleeve component. The spun bond nonwoven fabric has a relative hardness of 40~50 mm in an MD-direction, 20~37 mm in a CD-direction as measured by the cantilever method and a basis weight of 15~30 g/m². The respective barrier flaps are provided in their sealing surface zones with elastic members secured under tension thereto.

16 Claims, 3 Drawing Sheets

DISPOSABLE DIAPER

BACKGROUND OF THE INVENTION

This invention relates to a disposable diaper for absorption and containment of urine and other body exudates.

Japanese Patent Publication Gazette (Kokoku) No. Hei3-80502 discloses a disposable diaper comprising a liquid-pervious topsheet, a liquid-impervious backsheet, a liquid-absorbent core disposed between these two sheets and a pair of flexible barrier flaps which are stretchable and contractable under action of elastic members. Each of the barrier flaps comprises a branched portion extending upward from an inner side of the diaper and a sealing surface zone extending transversely from a top of the branched portion. The sealing surface zone consists of a first overhang extending inward and a second overhang extending outward respectively from the top of the branched portion. In this known diaper, normally the first overhang is elastically placed against a wearer's inguinal region and forms a pocket adapted to be opened inwardly so that this pocket may receive and contain loose passage and/or urine. The second overhang is elastically pressed around the wearer's leg to fasten the diaper around the wearer's leg and improves a leakage proof effect for body exudates.

The invention described in the Publication Gazette teaches that it is preferred to form the flaps at least partially by the material which has a high flexibility, breathability and liquid-impermeability. As examples of such material, a nonwoven fabric, an apertured plastic film and a laminate of these two materials are described, but none of further specific examples is described. Practically, the spun bond nonwoven fabric of polypropylene fibers has often been adopted as such nonwoven fabric.

From a viewpoint that the second overhang should be tightly pressed against the wearer's leg, the elastic members of a relatively high tensional stress are preferably used for the second overhang. On the other hand, the first overhang functions as a barrier flap and therefore it is required for the elastic members used in this overhang merely to contract sufficiently to rise the barrier flap and thereby to open the pocket. Also for the purpose of avoiding any apprehension that the first overhand might uncomfortably compress the wearer's skin, it is preferred to use the elastic members presenting a relatively low elongation stress in this first overhang.

SUMMARY OF THE INVENTION

In view of the problem as has been described above, it is an object of the invention to provide a disposable diaper having the barrier flaps which are sufficiently soft to allow the elastic members to smoothly contract in order that the elastic members of an elongation stress as low as possible can be used.

According to the invention, there is provided a disposable diaper having a basic diaper structure including a liquid-pervious topsheet, a liquid-impervious backsheet, a liquid-absorbent core disposed between the topsheet and the backsheet; a pair of side flaps extending outward along transversely opposite side edges of the absorbent core, and a pair of barrier flaps formed on an inner side of the diaper so that the barrier flaps rise on the inner side of the diaper, wherein:

each of the barrier flaps is made of a nonwoven fabric and includes a proximal end positioned on the inner side of the diaper, a risable wall extending upward from the proximal end, a sealing surface zone formed on a top of the risable wall so as to extend transversely of the diaper and a plurality of elastic members extending longitudinally of the barrier flap and secured under tension to the sealing surface zone; and the nonwoven fabric forming the barrier flap is a spun bond nonwoven fabric made of wich/sleeve type conjugated fibers including a sleeve component of polyethylene and a wick component of thermoplastic synthetic resin other than polyethylene, and the spun bond nonwoven fabric has a fineness of 1~3 d, a relative hardness of 40~50 mm in an MD-direction and 20~37 mm in a CD-direction as measured by the cantilever method and a basis weight of 15~30 g/m².

According to one embodiment of this invention, the wick of the conjugated fibers is made of thermoplastic synthetic resin selected from polypropylene and polyester.

According to another embodiment of this invention, the MD-direction of the nonwoven fabric coincides with a longitudinal direction of the barrier flaps.

DETAILED DESCRIPTION OF THE PREFERRED EMBODIMENTS

Details of a disposable diaper according to this invention will be more fully understood from the description given hereunder with reference to the accompanying drawings.

Figure 1:
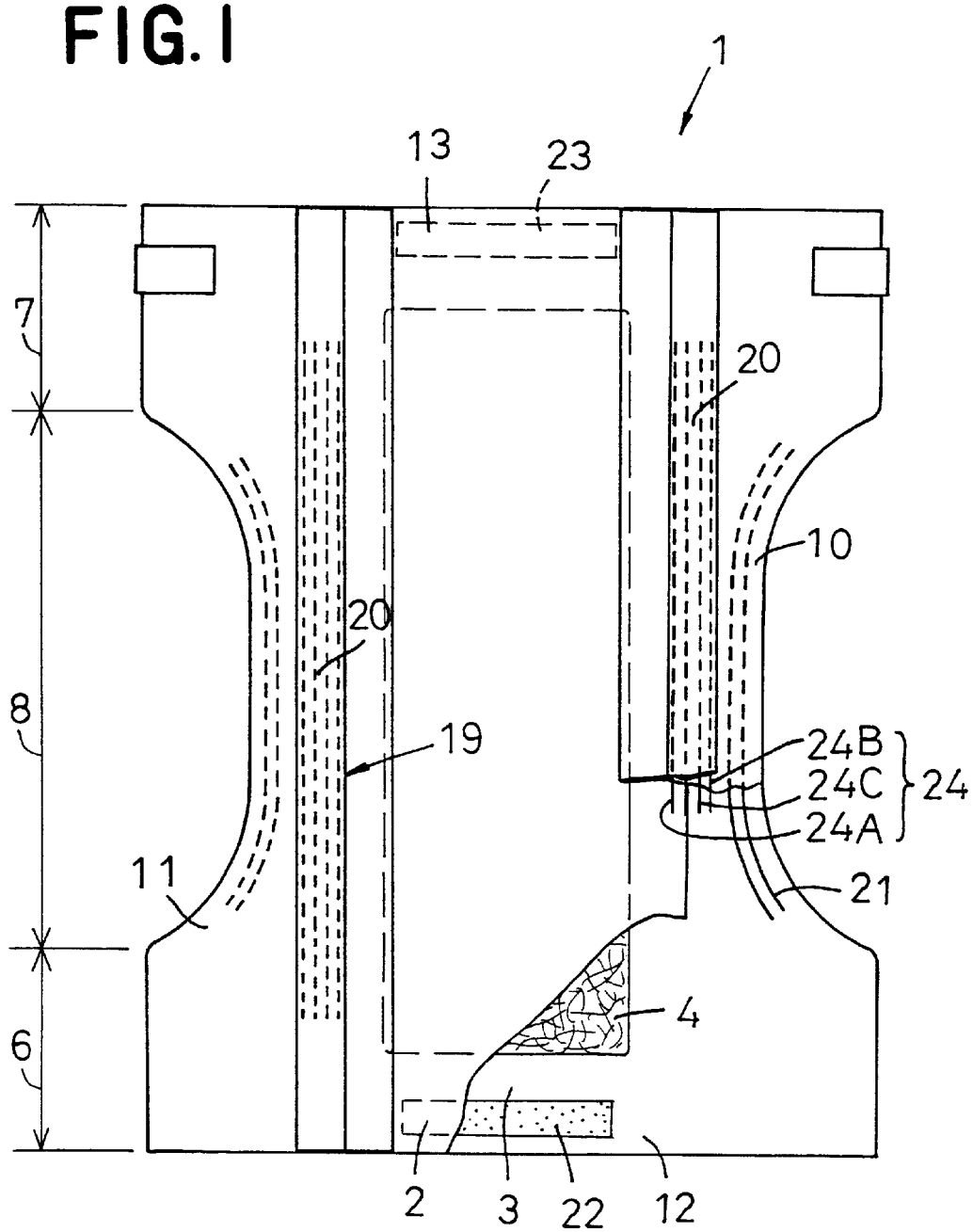
FIG. 1 is a plan view showing a partially cut away disposable diaper according to this invention in its developed state.
Figure 2:
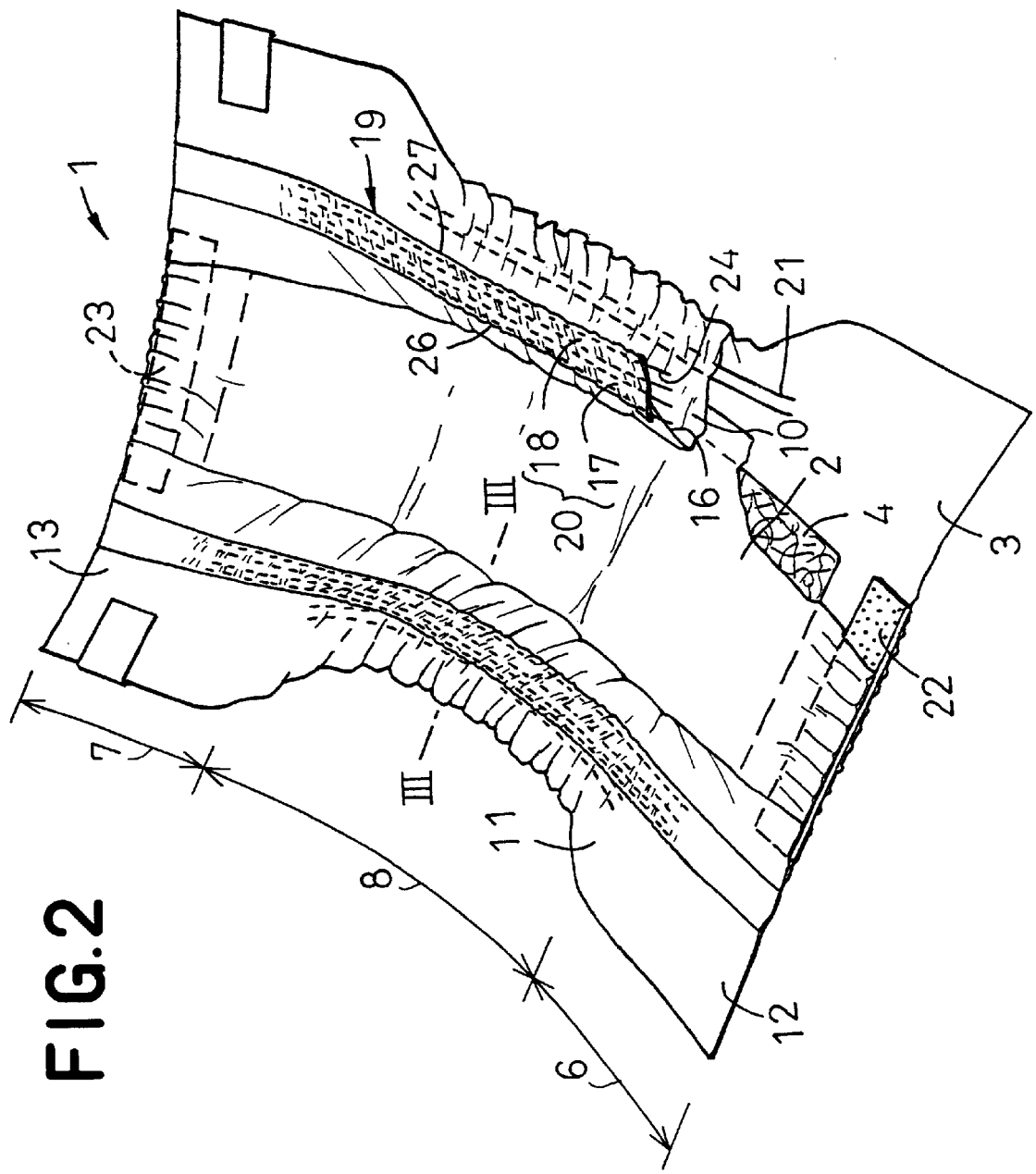
FIG. 2 is a perspective view showing the partially cut away diaper in its slightly curved state.

FIG. 1 is a plan view showing a partially cut away disposable diaper 1 and FIG. 2 is a perspective view showing the partially cut away diaper. In FIG. 2, the diaper is in its curved state under contraction of respective elastic members as will be described.

A diaper 1 comprises a liquid-pervious topsheet 2, a liquid-impervious backsheet 3 and a liquid-absorbent core 4 disposed between these two sheets 2, 3 so as to define a front waist region 6, a rear waist region 7 and a crotch region 8. Portions of topsheet 2 and the backsheet 3 extending outward beyond transversely opposite side edges of the absorbent core 4 are bonded together along peripheral edges of the absorbent core to form a pair of side flaps 11, 11 and longitudinally opposite end flaps 12, 13. Each of the side flaps 11, 11 is formed on its upper side with a barrier flap 19 extending across the crotch region 8 into the front and rear waist regions 6, 7. The barrier flap 19 comprises a risable wall 16 and a sealing surface zone 20 formed on an upper end of the risable wall 16. The sealing surface zone 20 comprises, in turn, a first overhang 17 extending inwardly of the diaper and a second overhang 18 extending outwardly of the diaper. The respective front and rear ends of these first and second overhangs 17, 18 are bonded to an inner surface of the diaper 1.

In the crotch region 8, each of the side flaps 11, 11 is provided with a plurality of elastic members 21 extending longitudinally of the side flap 11 and adapted to surround each of wearer's legs. These elastic members 21 are disposed between the topsheet 2 and the backsheet 3 or between the backsheet 3 and a sheet 10 forming the barrier flap 19 as shown and bonded under tension to an inner surface of at least one of these sheets.

The front and rear end flaps 12, 13 are provided with elastic member 22, 23 made of foamed polyurethane and extending circumferentially of these front and rear end flaps 12, 13, respectively. These elastic member 22, 23 are disposed between the topsheet 2 and the backsheet 3 and intermittently bonded under tension in a circumferential direction to respective inner surfaces of the topsheet 2 and the backsheet 3. Each of the sealing surface zones 20 is 5~30 mm wide and provided with a plurality of elastic members 24 extending across the crotch region 8 into the front and rear waist regions 6, 7 and bonded under tension to the sealing surface zone 20.

Figure 3:
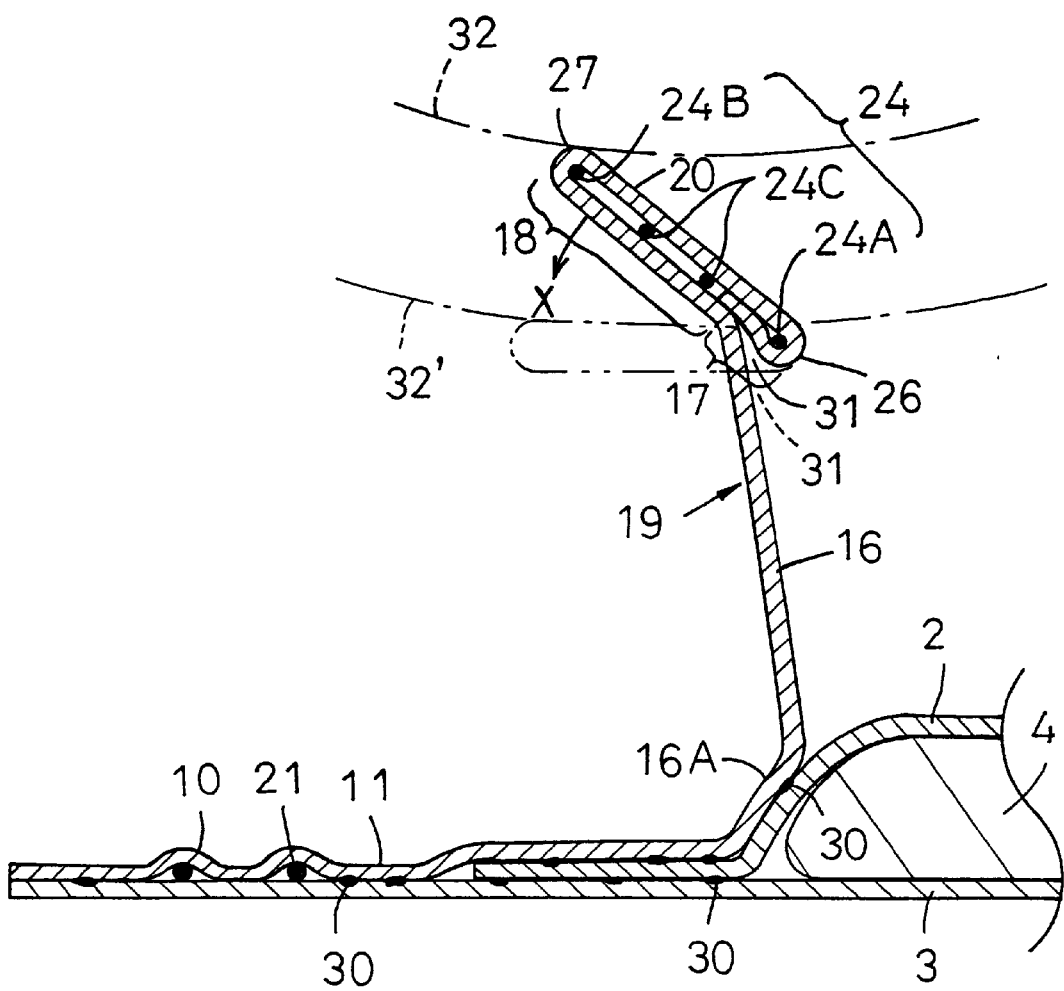
FIG. 3 is a fragmentary sectional view taken along a line III—III in FIG. 2.

FIG. 3 is a fragmentary sectional view taken along a line III—III. The elastic members 24 associated with each of the sealing surface zones 20 comprise a first elastic member 24A longitudinally extending along an inner side edge 26 of the first overhang 17, a second elastic member 24B longitudinally extending along an outer side edge 27 of the second overhang 18 and third elastic members 24C lying between the outer side edge 27 and a top of the risable wall 16 and longitudinally extending. While it is also possible to associate a plurality of first elastic members 24A with the first overhang 17, if a single elastic member 24A is provided as in the case illustrated, this first elastic member 24A should lie in the vicinity of the top of the risable wall 16, preferably in a range of 0~10 mm and more preferably in a range of 0.5~7 mm from the top. The risable wall 16 has a proximal end 16A at which the risable wall 16 rises on the inner side of the diaper 1 under contraction of the elastic member 24.

As viewed in FIG. 1 showing the diaper 1 in its longitudinally developed state, the first and second elastic members 24A, 24B extend between the respective front and rear ends of the first and second overhangs 17, 18 and their lengths are substantially equal to each other. The first elastic member 24A preferably has an elongation stress higher than that of the second elastic member 24B, more preferably has an elongation stress as well as an elongation percentage higher than those of the second elastic member 24B. Each of the third elastic members 24C has a length substantially equal to or smaller than those of the first and second elastic members 24A, 24B. Each of the third elastic members 24C preferably has an elongation stress equal to or lower than that of the second elastic member 24B and an elongation percentage equal to or higher than that of the second elastic member 24B. Preferably, a total elongation stress of these first, second and third elastic members 24A, 24B, 24C is sufficient to erect the barrier flap 19 as the diaper 1 is curved and corresponds to 30~80% of a total elongation stress of the elastic members 21 adapted to surround each of the wearer's legs. A total elongation stress of the barrier flap 19 exceeding such level would undesirably cause the sealing surface zone 20 to be pressed against the wearer's inguinal soft skin.

The topsheet 2 and the backsheet 3 are liquid-tightly bonded to each other along their portions extending outward the peripheral edge of the absorbent core 4 by means of hot melt adhesive 30. The backsheet 3 extends further outward beyond the side edges of the topsheet 2 and is bonded, preferably in a liquid-tight manner, along its extension beyond the topsheet 2 to the sheet 10 forming the barrier flap 19 by means of the hot melt adhesive 30. The sheet 10 extends inwardly of the diaper 1 so as to overlie the topsheet 2 and is bonded, preferably in a liquid-tight manner to the topsheet 2 by means of the hot melt adhesive 30. The elastic-members 21 adapted to surround the wearer's legs are disposed between the backsheet 3 and the sheet 10.

The barrier flaps 19 arranged as has been described above are flattened on the inner side of the diaper 1 as the first, second and third elastic members 24A, 24B, 24C are stretched by developing the diaper 1 in its longitudinal direction (See FIG. 1). As the diaper 1 is then curved in its longitudinal direction with the topsheet 2 lying inside, the risable wall 16 of the respective barrier flaps 19 rise on the respective side edge flaps 11 under contractile forces substantially of the first and second elastic members 24A, 24B (See FIG. 2). At the same time, the sealing surface zones 20 tilt with the respective first overhangs 17 being lowered (See FIG. 3). The third elastic members 24C contract and serve to prevent the sealing surface zones 20 from slackening between the respective first and second elastic members 24A, 24B. Thereupon, each of the first overhangs 17 cooperates with the risable wall 16 associated with this first overhang 17 to form a pocket 31 adapted to be opened downward and inwardly of the diaper 1. In this state, a plurality of gathers appear at least top surfaces of the respective sealing surface zones 20.

With the diaper 1 put on the wearer's body, the barrier flaps 19 rise on the inner side of the diaper 1 so that the sealing surface zones 20 can fit along their outer side edges 27 to the wearer's legs 32 indicated by imaginary lines. As the outer side edges 27 are further pressed against the legs, the sealing surface zones 20 are swung in a direction indicated by an arrow X around the respective first elastic members 24A having the highest elongation stress. As a result the sealing surface zones 20 fit the wearer's legs 32' over the larger areas and, at the same time, the respective pockets 31 are fully opened. Though not illustrated, the respective side flaps 11 tightly fit the legs 32' outside the respective barrier flaps 19.

The diaper 1 arranged as has been described above allows an amount of body exudates flowing in the transverse direction to be intercepted by the barrier flaps 19 and thereby to be prevented from leaking sideways. An amount of body exudates flowing upward along the risable walls 16 of the respective barrier flaps 19 to their tops is intercepted by the lower surfaces of the respective first overhangs 17 and thereby prevented from flowing into gaps defined between the legs 32 and the sealing surface zones 20. Should a certain amount of body exudates have flown into these gaps, such body exudates can scarcely flow over the barrier flaps 19 so far as the adequately large sealing surface zones 20 of the respective barrier flaps 19 fit around the wearer's legs or inguinal regions as indicated by imaginary lines. With the diaper 1 according to this invention, a leakage of body exudates can be effectively alleviated by the barrier flaps 19 functioning in such a manner.

According to an alternative embodiment, each of the first overhangs 17 may be provided with a plurality of elastic members 24A extending in parallel to each other. These elastic members 24A are preferably identical one to another as length and elongation percentage are concerned and the elongation stress is preferably adjusted so that the nearer the elastic members 24A is positioned the inner side edge 26, the higher the elongation stress of the respective elastic members 24A is. If it is not essential to avoid slackening of the sealing surface zone 20, the third elastic member 24C may be eliminated.

To ensure that the elastic members 24A~24C can easily contract and the barrier flaps 19 can fully rise even when a total elongation stress of these first~third elastic members 24A~24C is a relatively low, adequately nonwoven fabric is used as the sheet 10 forming the barrier flaps 19. A preferable example of such nonwoven fabric is a spun bond nonwoven fabric comprising conjugated fibers of polyethylene-sleeved wick/sleeve type. This nonwoven fabric has a basis weight of 15~30 g/m² and a fineness of 1~3 d. Relative hardness of this nonwoven fabric is 40~50 mm in an MD-direction and 20~27 mm in a CD-direction during its manufacturing process as measured by the cantilever method (A-method) according to JIS (Japanese Industrial Standard) L-1. Such nonwoven fabric is preferably used so that the MD-direction of the nonwoven fabric should coincide with the longitudinal direction of the barrier flaps 19. In this manner, the barrier flaps 19 can rise more smoothly than when the CD-direction coincides with the longitudinal direction. Wick material of the conjugated fibers is thermoplastic synthetic resin such as polypropylene or polyester.

The barrier flaps 19 made of such nonwoven fabric advantageously do not obstruct smooth contraction of the first~third elastic members 24A~24C and, upon contraction of these elastic members 24A~24C, can form a plurality of gathers which are finer than those formed by the conventional barrier flaps having a higher relative hardness and made from a nonwoven fabric of polypropylene or polyester fiber. Even when such fine gathers contact the wearer's skin, there is no apprehension that any amount of body exudates might leak through gaps defined between the gathers' troughs and the wearer's skin since these gaps are minimized. Even when crests of respective gathers contact the wearer's skin, there is no apprehension that these crests might uncomfortably irritate the skin because the crest of each gather is sufficiently soft to protect the wearer's skin from such undesirable irritation.

Softness of the nonwoven fabric used as the stock material for the barrier flaps 19 can be expressed also in a bending stiffness determined, for example, by KES bending tester "KES FB-3" (KATO TECH Corp.) instead of the relative hardness measured by the cantilever method. While it is impossible to explain a correlation between these relative hardness and stiffness, it was found that a stiffness of the spun bond nonwoven fabric to be used as the stock material for the barrier flaps 19 is preferably in a range of 0.015~0.020 gf·cm²/cm in the MD-direction and in a range of 0.002 ~0.005 gf·cm²/cm in the CD-direction. Measurement of the stiffness was conducted also on the spun bond nonwoven fabric of polypropylene fibers which is similar to the nonwoven fabric of wick/sleeve type conjugated fibers so far as its basis weight of 15~30 g/m² and its fineness of 1~3 d are concerned. Such spun bond nonwoven fabric presented stiffness values as high as 0.045~0.052 gf·cm²/cm in the MD-direction and 0.012~0.017 gf·cm²/cm in the CD-direction.

For exploitation of this invention, a liquid-pervious nonwoven fabric or a porous plastic sheet may be used as the stock material for the topsheet 2. A liquid-impervious plastic sheet may be used as the stock material for the backsheet 3 and fluff pulp or a mixture of fluff pulp and superabsorptive polymer particles may be used as the stock material for the absorbent core 4. The respective elastic members used in the diaper 1 may be bonded to the sheet members by means of hot melt adhesive. To bond the sheet members to each other, in addition to the hot melt adhesive, the heat-sealing technique may be also used. For example, the nonwoven fabric forming the barrier flaps 19 is composed of wick/sleeve type conjugated fibers which contains, in turn, polyethylene having a relatively low melting point. Accordingly, such nonwoven fabric can be heat-sealed to the inner side of the diaper 1 at a relatively low temperature. The lower the heat-sealing temperature is, the smaller the heat energy to be consumed during the process of manufacturing the diaper 1 is and there is no apprehension that a relatively high temperature might damage the regions of the diaper 1 other than those to be intentionally subjected to the heat-sealing treatment.

With the disposable diaper according to this invention, the barrier flaps are formed by the nonwoven fabric of the conjugated fibers including polyethylene sleeve component. Such nonwoven fabric is soft so that a plurality of elastic members constituting the sealing surface zones of the respective barrier flaps are not prevented from smoothly contracting even if a total elongation stress of these elastic members is relatively low. Therefore, the barrier flaps can readily rise on the inner side of the diaper whereupon sufficiently fine gathers are formed thereon to prevent any amount of body exudates from leaking sideways. The crests of the individual gathers are adequately soft to protect the wearer's skin from undesirable irritation, conjointly with the low elongation stress of the elastic members.

What is claimed is:

1. A disposable diaper, including
a liquid-pervious topsheet, a liquid-impervious backsheet and a liquid-absorbent core disposed between said topsheet and said backsheet; and
a pair of barrier cuffs formed on a top surface of said diaper wherein:
each of said barrier cuffs is made of a nonwoven fabric and includes
a proximal end positioned on the top surface of said diaper;
a risable wall projecting upward from said proximal end;
a sealing surface zone formed on top of said risable wall so as to extend transversely of the diaper; and
a plurality of elastic members extending longitudinally of said barrier cuff and secured under tension to said sealing surface zone; and
the nonwoven fabric is spun bond nonwoven fabric made by combining a sleeve component of polyethylene and a wick component of a thermoplastic synthetic resin other than polyethylene into wick/sleeve type conjugated fibers, said spun bond nonwoven fabric has a stiffness of from about 0.015 to about 0.020 gf·cm²/cm in an MD-direction and from about 0.002 to about 0.005 gf·cm²/cm in a CD-direction of said spun bond nonwoven fabric, as measured by the KES bending tester KES FB-3.

2. The diaper according to claim 1, wherein the wick component of said conjugated fibers is made of at least one of polypropylene and polyester.

3. The diaper according to claim 1, wherein the MD-direction of said nonwoven fabric coincides with the longitudinal direction of said barrier cuffs.

4. A disposable absorbent article, comprising a liquid-permeable topsheet, a liquid-impermeable backsheet and a liquid-absorbent core disposed between said topsheet and said backsheet, said article having longitudinal and transverse directions and being formed with leg openings on transversely opposite side edges thereof;
said article further comprising a pair of longitudinally extending barrier cuffs each projecting upward from the topsheet while extending in an inwardly spaced relation to associated one of said leg openings between the core and said associated leg opening, each of said barrier cuffs including
a risable wall having a lower end attached to the topsheet and an upper end; and
a sealing member supported by the upper end of said risable wall and provided with first and second elastic members each extending and contractible in the longitudinal direction of said article, the second elastic member positioned closer, in the transverse direction of said article, to said associated leg opening than the first elastic member;

wherein the first elastic member has an elongation stress higher than that of the second elastic member.

5. The article of claim 4, wherein the first elastic member has an elongation percentage higher than that of the second elastic member.

6. The article of claim 4, wherein a distance between the first elastic member and the upper end of said risable wall is from about 0 to about 10 mm.

7. The article of claim 6, wherein said distance is from about 0.5 to about 7 mm.

8. The article of claim 4, wherein the first and second elastic members have substantially equal lengths in the longitudinal direction of said article.

9. The article of claim 4, wherein said sealing member is further provided with at least one third of the first and second elastic members extending and contractible in the longitudinal direction of said article and between the first and second elastic members.

10. The article of claim 9, wherein the third elastic member has a length equal to or smaller than those of the first and second elastic members.

11. The article of claim 9, wherein the third elastic member has an elongation stress equal to or lower than that of the second elastic member.

12. The article of claim 9, wherein the third elastic member has an elongation percentage equal to or higher than that of the second elastic member.

13. The article of claim 9, further comprising fourth elastic members extending along said leg openings, wherein a total elongation stress of the first, second and third elastic members is from about 30 to about 80% of an elongation stress of the fourth elastic member of said associated leg opening.

14. The article of claim 4, wherein said sealing member comprising first and second overhang portions extending inwardly and outwardly from the upper end of said risable wall, respectively, for accommodating the first and second elastic members, respectively.

15. The article of claim 14, wherein the first overhang portion and said risable wall together define a pocket opened downwardly and inwardly toward the core.

16. The article of claim 14, wherein the first elastic member includes a plurality of elastic strips extending longitudinally of said article and having substantially equal length and elongation percentage, said elastic strips further having elongation stresses which decrease corresponding to increasing distances, in the transverse direction of said article, from said elastic strips to the core.

* * * * *